US012161784B2

(12) United States Patent
Min et al.

(10) Patent No.: US 12,161,784 B2
(45) Date of Patent: Dec. 10, 2024

(54) SYSTEMS AND METHODS FOR VOLUME REDUCTION OF BLOOD PRODUCTS PRIOR TO TRANSFUSION

(71) Applicant: Fenwal, Inc., Lake Zurich, IL (US)

(72) Inventors: Kyungyoon Min, Kildeer, IL (US); James Madsen, Chicago, IL (US); Thomas Gniadek, Deerfield, IL (US)

(73) Assignee: Fenwal, Inc., Lake Zurich, IL (US)

( * ) Notice: Subject to any disclaimer, the term of this patent is extended or adjusted under 35 U.S.C. 154(b) by 102 days.

(21) Appl. No.: 17/937,603

(22) Filed: Oct. 3, 2022

(65) Prior Publication Data

US 2023/0108077 A1 Apr. 6, 2023

Related U.S. Application Data

(60) Provisional application No. 63/252,417, filed on Oct. 5, 2021.

(51) Int. Cl.
*A61M 1/02* (2006.01)

(52) U.S. Cl.
CPC .......... *A61M 1/029* (2013.01); *A61M 1/0218* (2014.02); *A61M 1/024* (2013.01); *A61M 1/0281* (2013.01); *A61M 2202/0427* (2013.01); *A61M 2202/0429* (2013.01)

(58) Field of Classification Search
CPC .. A61M 1/029; A61M 1/0218; A61M 1/0281; A61M 2202/0427; A61M 2202/0429; A61M 1/024; A61M 1/0259; A61M 1/0271
See application file for complete search history.

(56) References Cited

U.S. PATENT DOCUMENTS

| | | | | |
|---|---|---|---|---|
| 5,194,145 A | * | 3/1993 | Schoendorfer | A61M 1/3496 210/651 |
| 5,215,519 A | * | 6/1993 | Shettigar | A61M 1/3403 604/6.1 |
| 5,858,238 A | * | 1/1999 | McRea | B01D 61/145 210/651 |
| 6,582,386 B2 | * | 6/2003 | Min | A61M 1/3692 604/6.11 |
| 6,884,228 B2 | * | 4/2005 | Brown | A61M 1/3696 210/782 |
| 9,402,866 B2 | | 8/2016 | Radwanski et al. | |
| 2003/0229302 A1 | * | 12/2003 | Robinson | A61M 1/0218 604/4.01 |
| 2009/0211962 A1 | * | 8/2009 | Min | A61M 1/0218 210/378 |
| 2012/0225419 A1 | * | 9/2012 | Min | A61M 1/0209 422/44 |

(Continued)

OTHER PUBLICATIONS

Extended European Search Report for European Application 22199537.6 mailed on Feb. 8, 2023.

*Primary Examiner* — Benjamin J Klein
(74) *Attorney, Agent, or Firm* — Cook Alex Ltd.

(57) ABSTRACT

Methods and systems for transfusing reduced-volume blood components are disclosed. Previously collected blood components are introduced into a fluid circuit associated with an apparatus that further separates the component into a reduced volume component and supernatant. The reduced-volume blood component is transfused to the patient in need of the component without the risk of circulatory overload.

9 Claims, 10 Drawing Sheets

(56) References Cited

U.S. PATENT DOCUMENTS

| | | | |
|---|---|---|---|
| 2013/0004937 A1* | 1/2013 | Yoshida | B01D 19/0031 |
| | | | 435/2 |
| 2013/0220925 A1 | 8/2013 | Min et al. | |
| 2013/0334139 A1* | 12/2013 | Blickhan | B01D 61/18 |
| | | | 210/85 |
| 2014/0066281 A1* | 3/2014 | Weasler | A61J 1/2093 |
| | | | 494/37 |
| 2014/0069868 A1* | 3/2014 | Nguyen | A61M 1/36224 |
| | | | 210/196 |
| 2014/0263065 A1* | 9/2014 | Samolyk | A61M 1/3667 |
| | | | 137/1 |
| 2014/0378290 A1* | 12/2014 | Kimura | A61M 1/3696 |
| | | | 494/35 |
| 2015/0119795 A1* | 4/2015 | Germain | A61M 1/34 |
| | | | 604/28 |
| 2016/0144098 A1* | 5/2016 | Radwanski | A61M 1/3692 |
| | | | 210/651 |
| 2019/0184076 A1* | 6/2019 | Gourlay | F04B 9/14 |
| 2022/0409780 A1* | 12/2022 | Rebulla | A61M 1/3693 |

* cited by examiner

SYSTEMS AND METHODS FOR VOLUME REDUCTION OF BLOOD PRODUCTS PRIOR TO TRANSFUSION

CROSS-REFERENCE TO RELATED APPLICATION

This application claims the benefit of and priority to U.S. Provisional Patent Application Ser. No. 63/252,417, filed on Oct. 5, 2021, the disclosure of which is incorporated herein by reference in its entirety.

FIELD OF THE DISCLOSURE

The present disclosure is directed to the processing, collection, and transfusion of blood components. More particularly, the present disclosure is directed to the infusion/transfusion of a reduced-volume blood component to avoid circulatory overload in the patient receiving the transfusion of the blood component.

BACKGROUND

The administration/transfusion of blood and/or blood components is common in the treatment of patients suffering from disease or blood loss. Rather than infuse whole blood, however, it is more typical and economical that individual components be administered to the patient in need.

Whole blood is made up of various cellular components such as red cells, white cells and platelets suspended in its liquid component, plasma. Whole blood can be separated into its constituent components (cellular or liquid), and the desired separated component can be administered to a patient in need of that particular component.

For example, administration (transfusion) of platelets is often prescribed for cancer patients whose ability to make platelets has been compromised by chemotherapy. Red blood cells are typically administered to patients who have suffered a loss of blood, anemia or other disorders. Infusion of plasma may also be prescribed for therapeutic reasons and, more recently, the harvesting and administration of stem cells has received widespread interest within the medical community.

Transfusion of an excess volume of a blood component can lead to Transfusion-associated circulatory overload (TACO). TACO is a serious transfusion complication which may be caused by a rapid transfusion of blood products. TACO is defined as acute pulmonary edema due to circulatory overload within 6-12 hours of transfusion. Currently, TACO is prevented by avoiding unnecessary transfusions and by transfusing smaller volumes of blood at slower rates. If TACO is suspected, the transfusion is halted and the patient is treated with oxygen, diuretics and other treatments for heart failure.

It would be desirable to avoid TACO altogether, without the need for remedial treatments as described above. It would also be desirable to reduce the total volume of the transfusion by removing the supernatant, i.e., plasma or an additive solution such as a platelet additive solution (PAS) or a red blood cell additive solution commonly used in the storage of collected blood components, before transfusion. In this manner, the patient receives the needed blood components (red blood cells, platelets, etc.) without extra supernatant fluid volumes.

SUMMARY

There are several aspects of the present subject matter which may be embodied separately or together in the methods and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, the present disclosure is directed to a method for transfusing a blood component to patient. The method includes accessing the vascular system of a patient with a needle that is in flow communication with a disposable fluid circuit. The circuit is mounted on an apparatus including a first pump, a second pump and a separation drive unit. The fluid circuit includes a container of priming solution, a waste container and a final reduced-volume blood component container and a separation chamber configured for mounting on the separation drive unit of the apparatus. The method further includes attaching a container of a previously collected blood component to the disposable fluid circuit and first introducing a priming solution from the container of priming solution into at least a portion of said fluid circuit including the separation chamber.

Once the fluid circuit has been primed, the method includes pumping the collected blood component from the container holding the previously collected blood component into at least a portion of the fluid circuit including the separation chamber and separating the collected blood component into a reduced-volume blood component and a supernatant component in the separation chamber.

In accordance with the method, the separated supernatant is collected in the waste container and the volume-reduced collected blood component is collected in the final reduced volume blood component container. The method further includes opening a flow path between the final blood component container and the vascular system of the patient and delivering the volume-reduced collected blood component to the patient.

In another aspect of the present disclosure, a system for transfusing a reduced-volume blood component to a patient includes a reusable separation and transfusion apparatus including a first pump, a second pump and a separator drive unit. A disposable fluid circuit is associated with the reusable separation and transfusion apparatus, the fluid circuit including a vascular access device, a separation chamber, a final product container, a supernatant container and tubing defining flow paths between the containers of a priming solution and collected blood component.

DETAILED DESCRIPTION OF THE EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
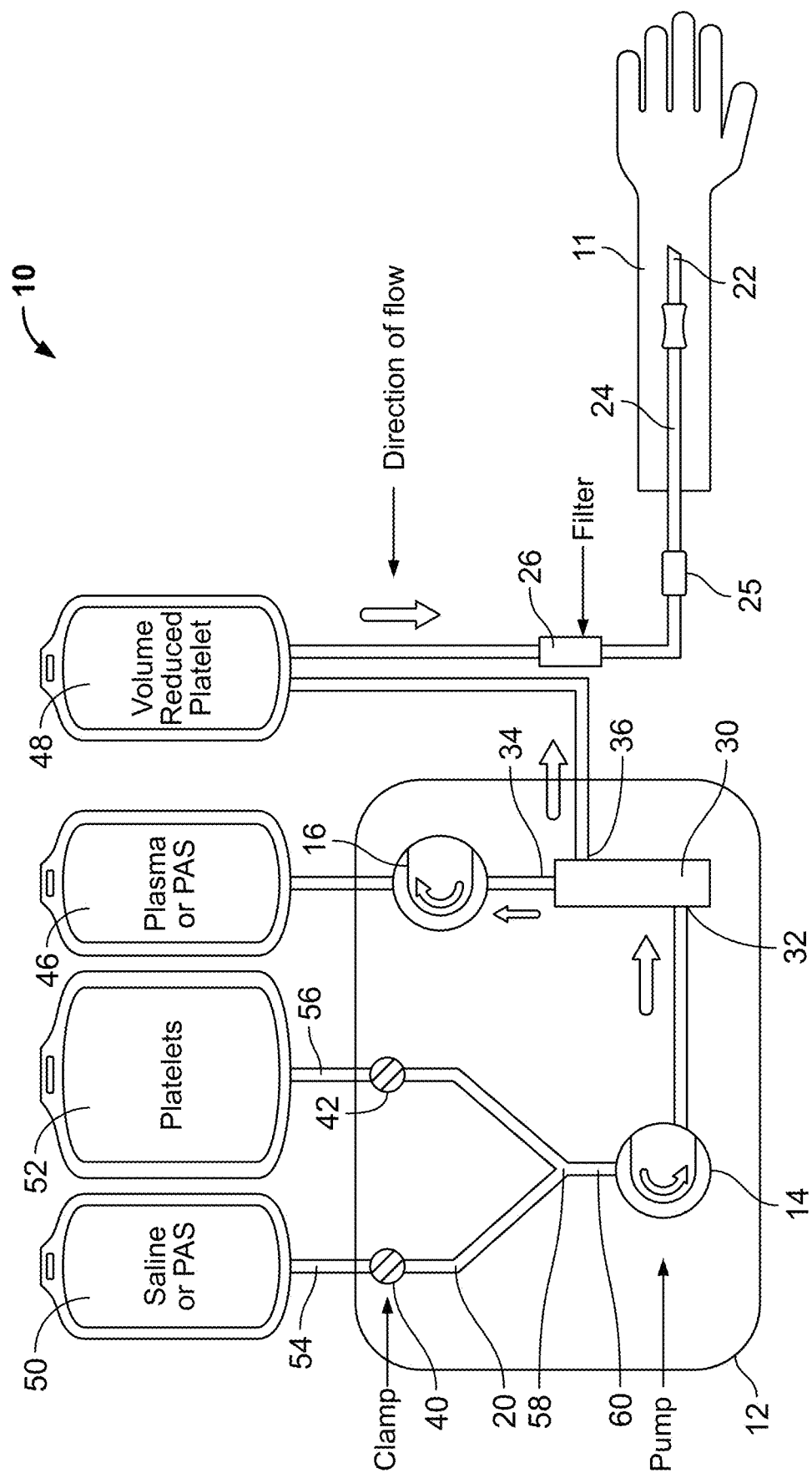
FIG. 1 is a schematic view of the system described herein as used for the processing and infusion of blood platelets.

FIG. 1 shows a system 10 for processing a previously collected blood component and for infusing a volume-reduced amount of the blood component to a patient 11. As shown in FIG. 1, system 10 includes a reusable apparatus 12 that includes a first pump 14, a second pump 16 and a separator drive unit which receives a separation chamber of a disposable fluid circuit described below. Apparatus 12 may be of compact design, suitable for placement next to or near the chairside or bedside of the patient 11 receiving the infusion. Pumps 14 and 16 may be peristaltic pumps configured to receive tubing segments of the fluid circuit, although other types of pumps may be used instead. Apparatus 12 may also include clamps which are likewise configured to receive tubing segments and are capable of opening and closing and thereby automatically control fluid flow through the tubing segments. Alternatively, the clamps may be manually operated clamps, such as roller clamps or Roberts-type clamps that are associated with the disposable fluid circuit.

Operation of pumps 14 and 16, separation drive unit and automatically-operated (i.e., non-manual) clamps (if present) is controlled by a control unit (controller). The controller may, according to the embodiments, include a programmable microprocessor, which microprocessor may be programmed to operate the blood processing device according to a process. The controller may be coupled to one or more of the structures of the blood processing device such as the aforementioned pumps, automated clamps and separator drive unit. The controller may receive information (e.g., in the form of signals) from these structures or to provide commands (e.g., in the form of signals) to these structures to control the operation of the structures. The controller may also be coupled to the scales, sensors, to provide commands to those devices to control their operation. The controller may be directly electrically connected to these structures to be coupled to them, or the controller may be directly connected to other intermediate equipment that is directly connected to these structures to be coupled to them.

Apparatus 12 may also include a user interface (not shown) such as a touchscreen or keypad which allows the operator to selectively control operation apparatus 12, including initiation and termination of pump rotation, opening and closing of clamps, activation of the separation drive unit etc.

As noted above, system 10 also includes a disposable fluid circuit 20 that may be, at least in part, mounted onto apparatus 12 or otherwise associated with it. Disposable fluid circuit 20 includes interconnected tubing, pre-attached containers and/or attachment sites for attaching containers, and a patient access device such as a venipuncture needle 22 for accessing the vascular system of the patient 11. Needle 22 is connected to and in flow communication with inlet tube 24 which defines a flow path for the blood component to be infused to the patient 11. Inlet tube 24 may include a (manually-operated) clamp 25 upstream of needle 22 for controlling flow through inlet tube 24 to the patient 11. A filter 26 may also be included in fluid circuit 20 to filter leukocytes or other unwanted cells or particles from the blood component to be infused.

As seen in FIG. 1, disposable fluid circuit 20 includes a separator or separation chamber 30 for mounting onto a separation drive unit of apparatus 12. In one embodiment, the separator or separation chamber may be a spinning membrane separator of the type described in U.S. Pat. No. 5,194,145, incorporated herein by reference. Spinning membrane separator 30 includes an inlet 32 through which a previously collected blood component is introduced and two outlets 34 and 36 through which separated supernatant and the desired volume reduced blood component exit, respectively, separator 30. In that regard, the membrane of separator 30 includes pores sized such that the desired component does not pass through the membrane (and exits through port 36) while allowing supernatant to freely pass through the membrane (where it exits through port 34).

Where apparatus 12 does not include automatically operable clamps, fluid circuit may include manually operated clamps 40 and 42 located on the tubing segments and which squeeze the tubing to close the flow path within the tube.

Disposable fluid circuit 20 may be provided with pre-attached empty plastic containers for receiving the separated blood components from separator 30. In one embodiment, container 46 may be pre-attached to fluid circuit 20. Container 46 may be in flow communication with outlet 34 of separator 30 and associated with peristaltic pump 16. Empty container 48 may be pre-attached and in flow communication with outlet 36 of separator 30.

Other containers may be attached to fluid circuit 20 at the time of use. In one embodiment container 50 containing a solution useful for priming fluid circuit 20 may be attached, in a sterile manner, to fluid circuit 20. In an alternative embodiment, fluid circuit 20 may be provided as a kit with pre-filled container 50 pre-attached. Container 52 which includes a previously collected blood component may likewise be attached to fluid circuit 20 at the time of infusion. As with the container 50 of priming solution, attachment may proceed in a sterile manner as will be known to those of skill in the art.

As seen in FIG. 1, containers 50 and 52 may be attached to tubing segments 54 and 56 which join at branch portion (member) 58 located upstream of where tubing segment 60 is loaded onto draw pump 14. Thus, pump 14 draws priming solution and the previously collected blood component into fluid circuit 20 and separator 30, albeit in sequence as will be described in detail below.

The system shown in FIG. 1 is particularly well suited for the processing of previously collected platelets and the infusion of a volume-reduced platelet product to a patient. Similarly configured systems may be used to process and infuse different blood components, such as red blood cells, as will be described in connection with FIGS. 6-10. Still other types of blood components may be processed and infused using the systems and methods described herein. For purposes of illustration and not limitation, the processing and infusion of previously collected platelets and red blood cells will now be described.

Figure 2:
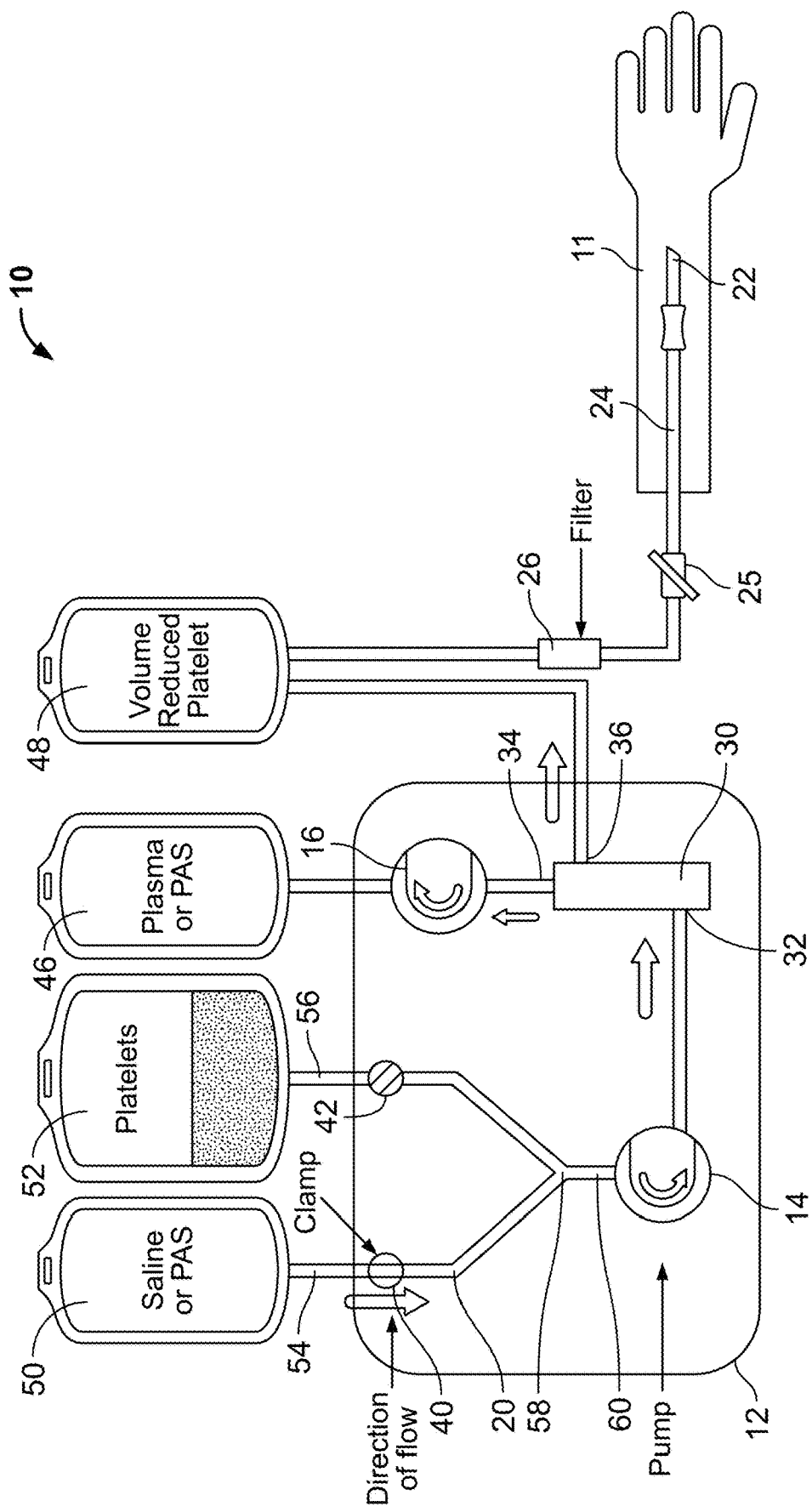
FIG. 2 is a schematic view of the system of FIG. 1 during priming of the fluid circuit.

FIG. 2 shows the system of FIG. 1 during the priming sequence in the processing and infusion of previously collected platelets. As shown in FIG. 2, container 50 which includes a priming solution is attached to fluid circuit 20. The priming solution may be any solution commonly used in the processing of blood components such as saline (0.9% NaCl) or a platelet additive solution (PAS) such as the solutions described in U.S. Pat. No. 9,402,866, the contents of which are incorporated herein by reference. As noted above, container 50 is attached to fluid circuit 20 in a sterile manner.

Also attached to fluid circuit 20 is a container 52 of previously collected platelets. Platelets are commonly collected from a donor using an apheresis device such as the AMICUS Separator, available from by Fenwal, Inc. of Lake Zurich, Ill., which is an affiliate of Fresenius Kabi AG of Bad Homburg, Germany. Platelet container 52 may contain one or more doses of platelets. Once the tubings of circuit 20 have been loaded onto pumps 14 and 16, the separator 30 mounted the separator drive unit and needle 22 inserted into the vein of the patient 11, the circuit 20 is ready to be primed. With clamp 25 and clamp 42 in a closed position and clamp 40 in an open position, pump 14 is activated (rotated) to draw priming solution from container 50 into the fluid circuit and into separator 30 through inlet 32. Separator 30 may be activated such that the spinning membrane is slowly rotated during the priming sequence. Pump 16 may likewise be activated to withdraw priming solution from the separator 30 and direct it to waste container 46. While most of the priming solution will be collected in container 46, some small amount of the priming solution may exit separator 30 through outlet port 36 and flow into container 48. Once the priming sequence has been completed, processing of the previously collected platelets may begin.

Figure 3:
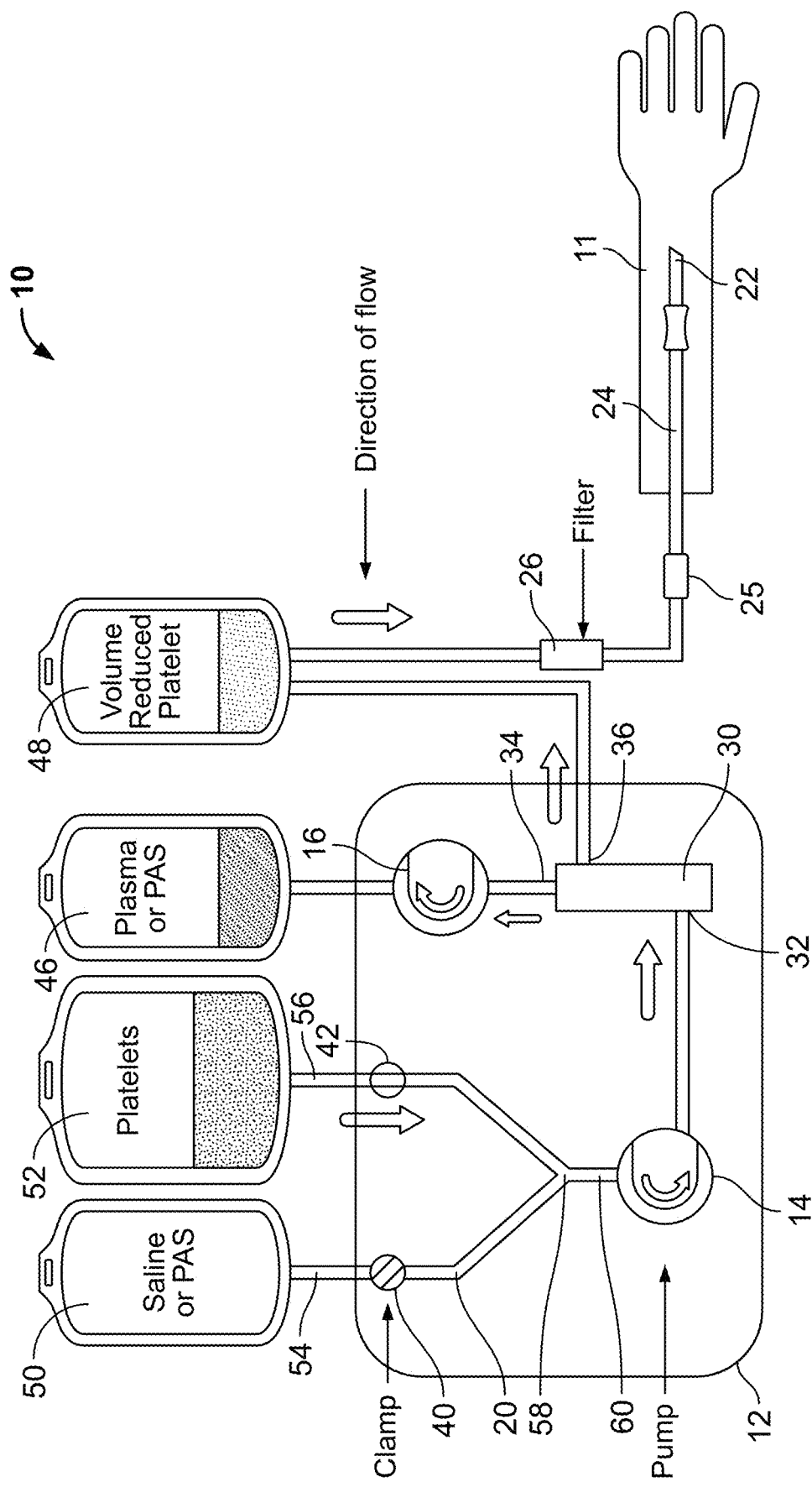
FIG. 3 is a schematic view of the system of FIG. 1 during the processing of previously collected platelets.

As shown in FIG. 3, in the platelet processing sequence, clamp 40 is now in the closed position while clamps 42 and 25 are in the open position. Pump 14 is now again activated to draw the previously collected platelets from container 50 into the now primed fluid circuit 20. Platelets are introduced into separator 30 through inlet 32 where they are separated into platelets and supernatant which may include plasma and previously added (for storage) PAS. The pores in membrane are sized such that separated platelets are not allowed to pass through the membrane. Instead, the platelets accumulate in the gap between the outer surface of the membrane and the inner surface of the separator housing, eventually exiting the separator through outlet 36 and flowing into "final" product container 48. Supernatant passes through the membrane and is pumped by pump 16 through outlet 34 and into waste container 46. During processing, clamp 25 is open and the volume-reduced platelets collected in container 48 begin to drain from container 48, passing through filter 26 and delivered to the patient 11.

Figure 4:
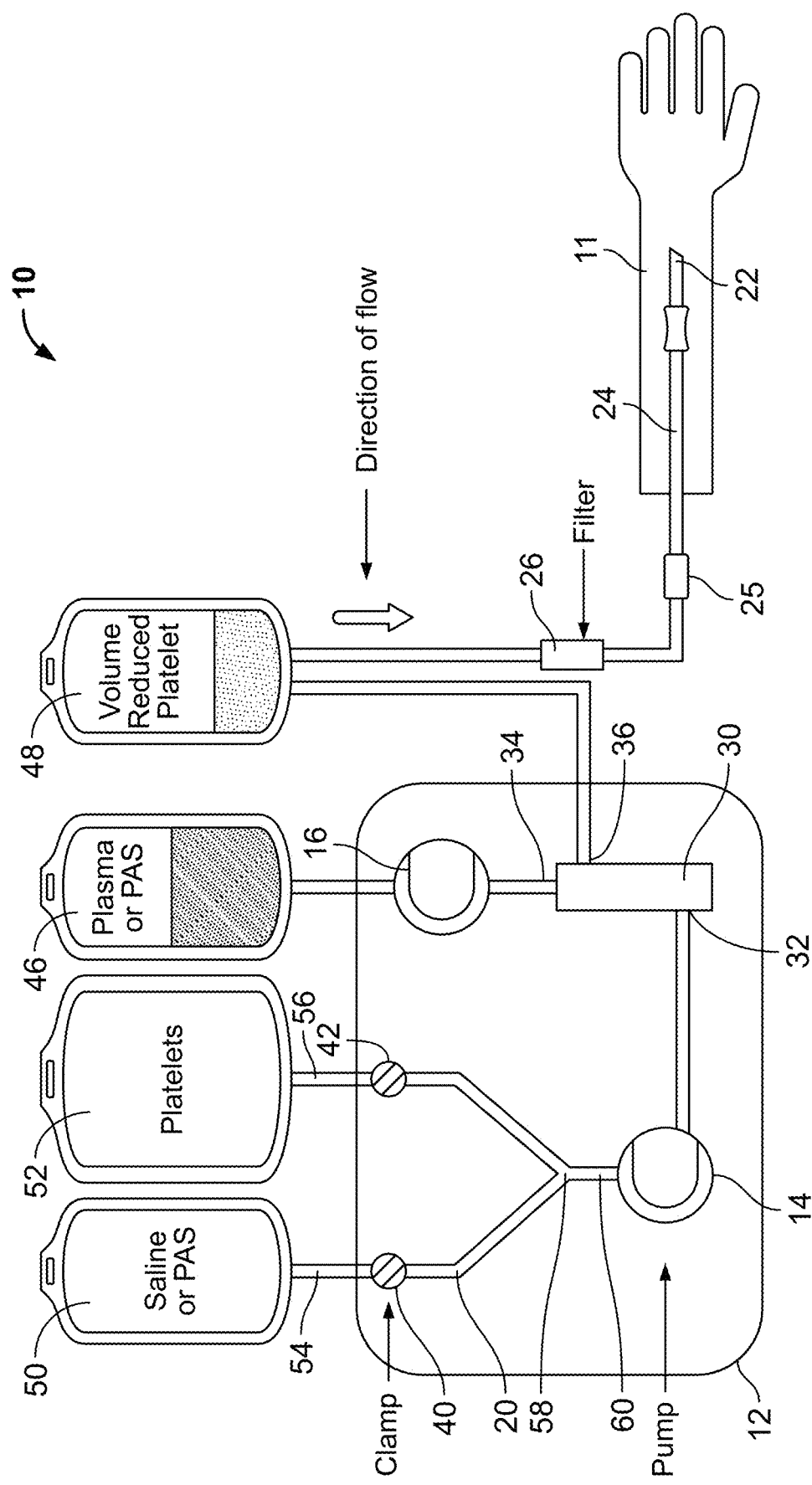
FIG. 4 is a schematic view of the system of FIG. 1 during the infusion of the volume-reduced platelets to the patient.
Figure 5:
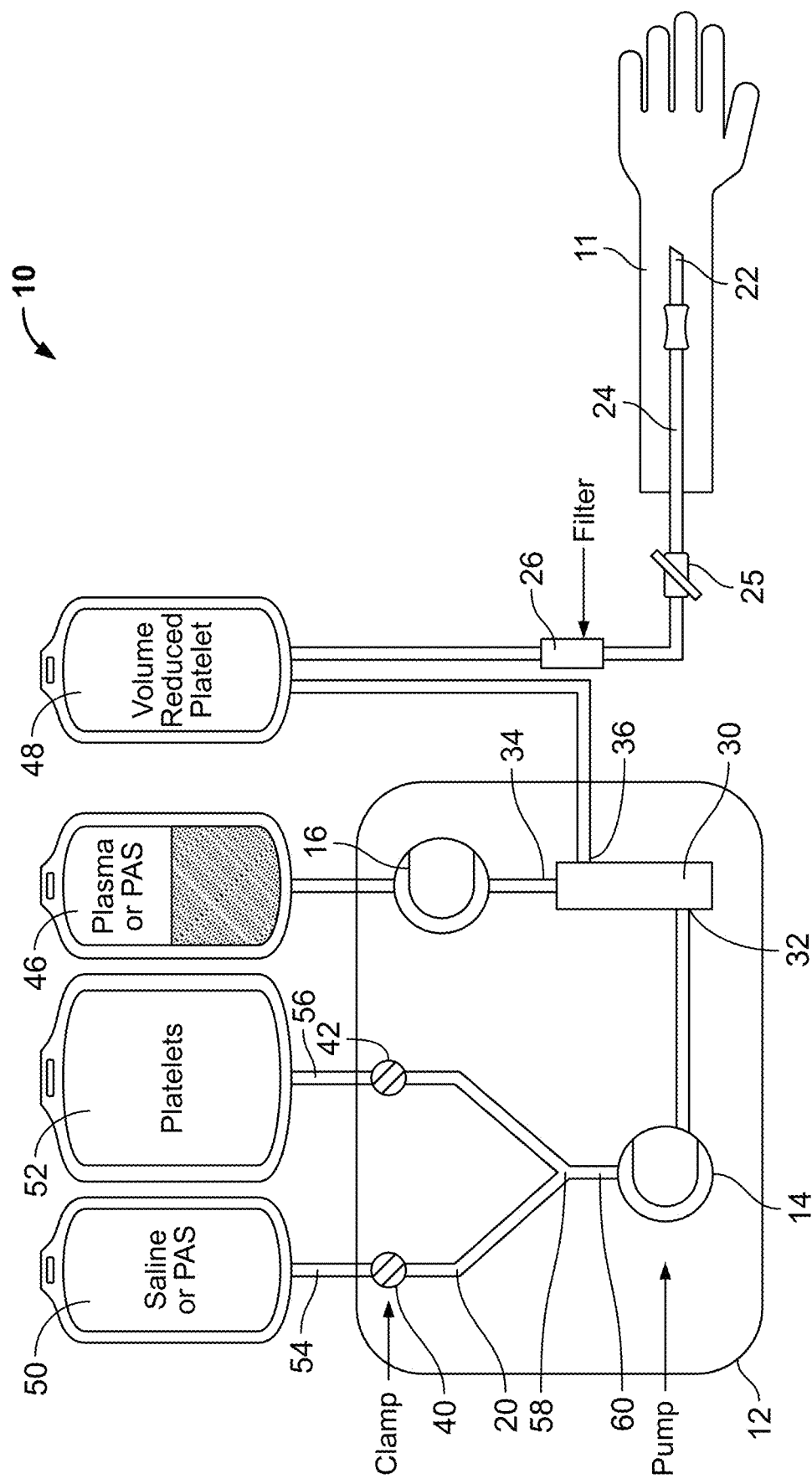
FIG. 5 is a schematic view of the system of FIG. 1 after infusion of the volume-reduced platelets has been completed.

Once the entire volume of previously collected platelets has been processed and container 52 is empty (which can be visually ascertained or determined by the change in weight of the container 52 which may be suspended from a weigh scale on apparatus 12), processing of the platelets from an original volume in container 52 to a reduced volume in container 48 is complete. As shown in FIG. 4, in this finishing phase, pumps 14 and 16 are turned off. With clamp 25 in an open position, a slow, gravity-fed infusion/transfusion of the reduced-volume platelets to the patient 11 which commenced during the previous processing phase continues. Once container 48 is empty as shown in FIG. 5, infusion/transfusion is complete. In one embodiment, the volume of platelets can be reduced, for example, from a starting volume of 300 ml to a transfusible, reduced volume of 100 ml, or more preferably 50 ml, or 30 ml.

Figure 6:
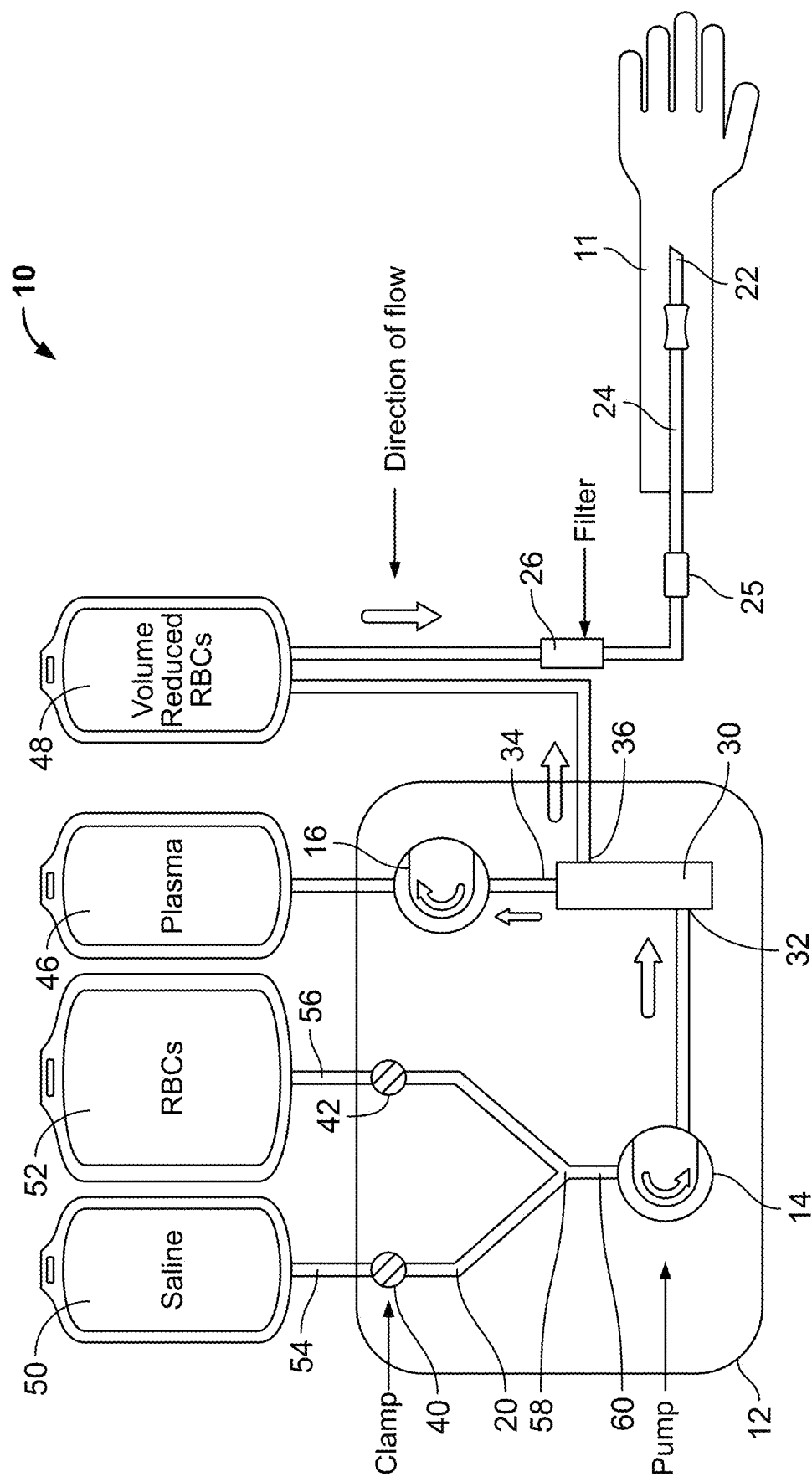
FIG. 6 is a schematic view of the system described herein as used for the infusion of red blood cells.

A reusable apparatus and associated fluid circuit of the type described above may also be used in the processing and infusion/transfusion of previously collected red blood cells. As seen in FIG. 6, a fluid circuit 20 is associated with reusable apparatus 12 as described above. Container 52 which holds previously collected red blood cells is attached in a sterile manner to fluid circuit 20.

Figure 7:
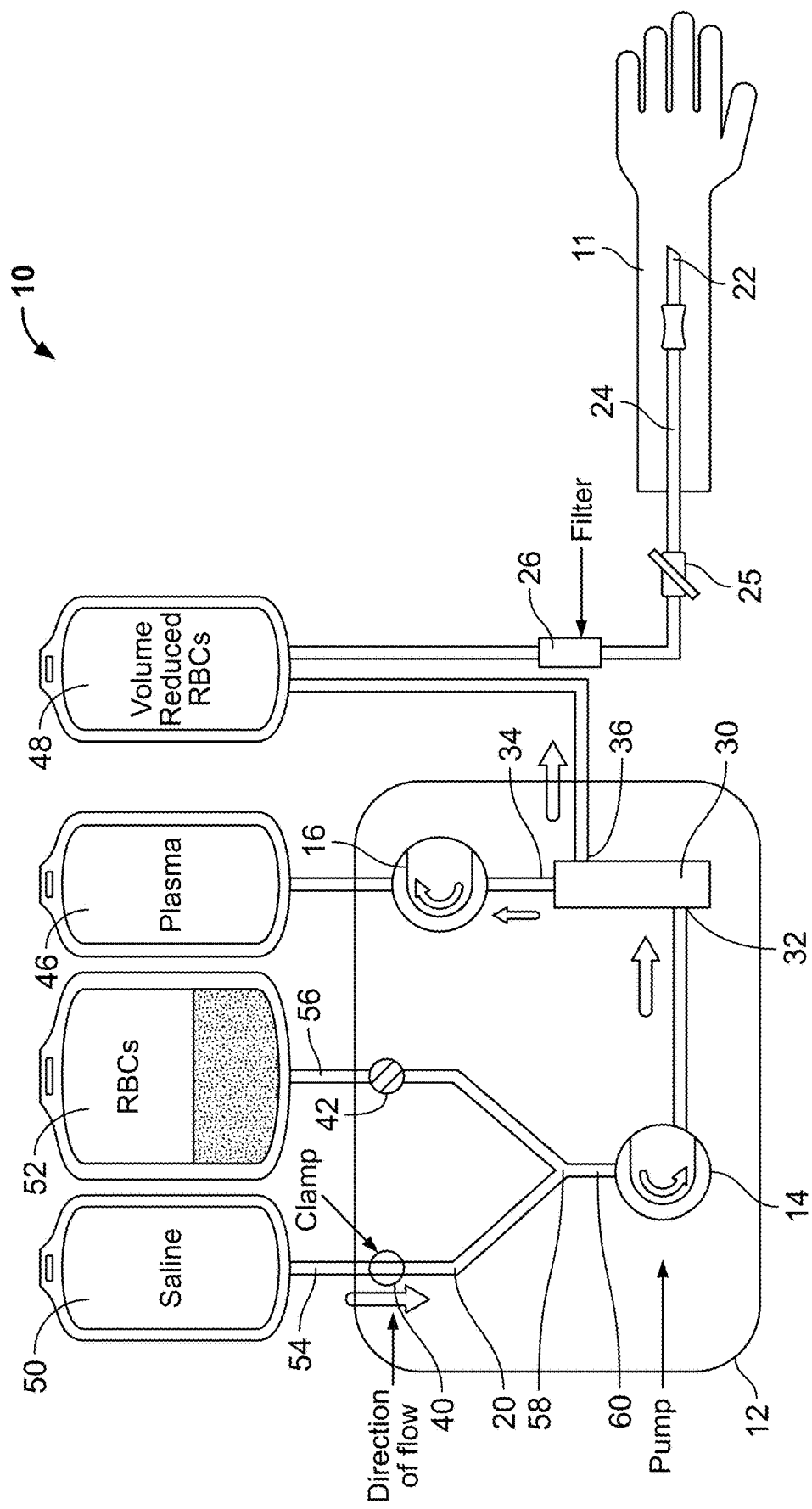
FIG. 7 is a schematic view of the system of FIG. 6 during priming of the fluid circuit.
Figure 8:
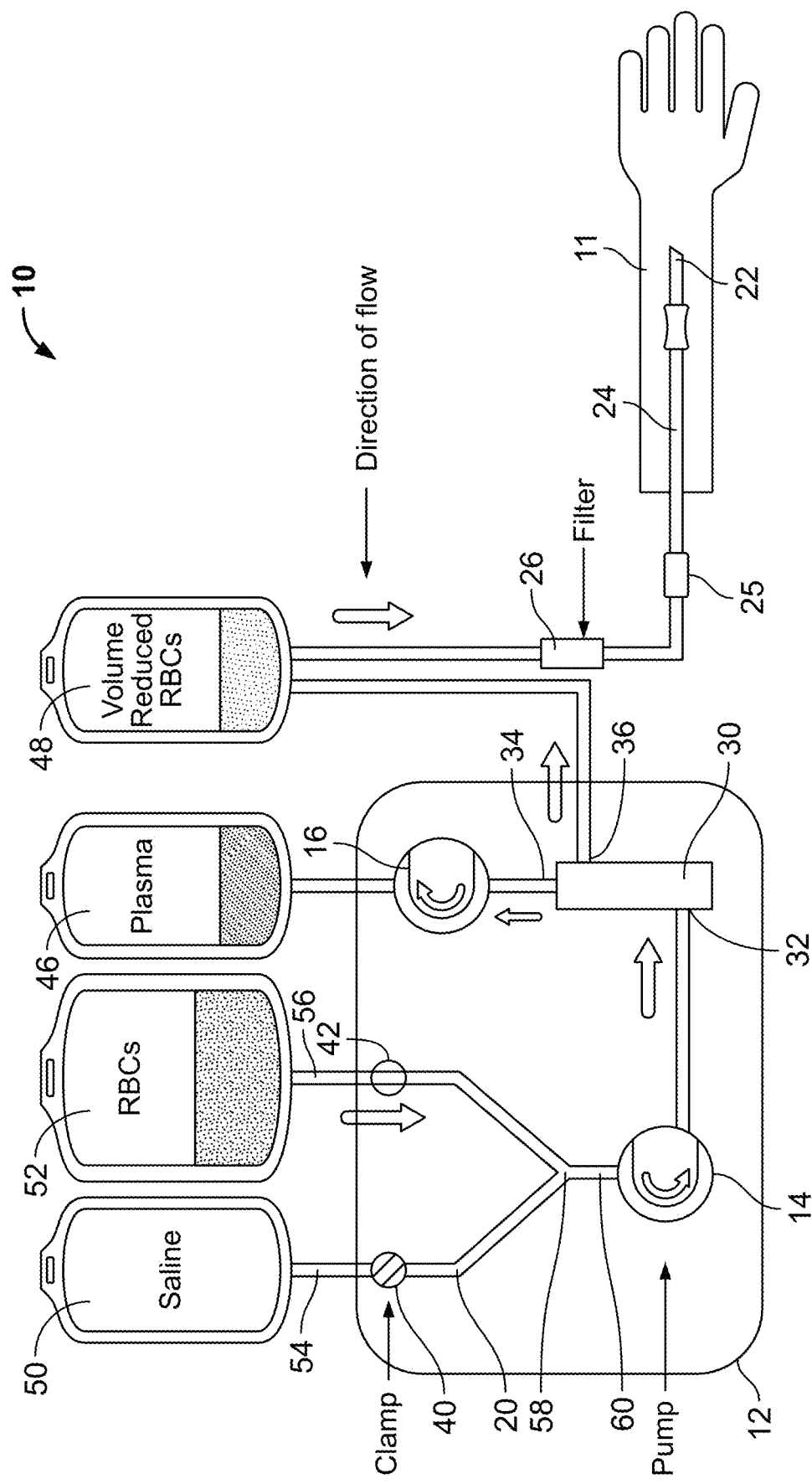
FIG. 8 is a schematic view of the system of FIG. 6 during the processing of previously collected red blood cells.

Once the tubings of circuit 20 have been loaded onto pumps 14 and 16, the separator 30 mounted the separator drive unit, and needle 22 inserted into the vein of the patient 11, the circuit 20 is ready to be primed. As shown in FIG. 7, with clamp 25 and clamp 42 in a closed position and clamp 40 in an open position, pump 14 is activated (rotated) to draw priming solution (e.g., saline) from container 50 into the fluid circuit and separator 30 through inlet 32. Separator 30 may be activated such that the spinning membrane is slowly rotated during the priming sequence. Pump 16 may likewise be activated to withdraw priming solution from the separator 30 and direct it to waste container 46. While most of the priming solution will be collected in container 46, some of the priming solution may exit separator 30 through outlet port 36 and flow into container. Once the priming sequence has been completed, processing the previously collected red blood cells may begin As shown in FIG. 8, in the red blood cell processing sequence, clamp 40 is now in the closed position while clamps 42 and 25 are in the open position. Pump 14 is now again activated to draw previously collected red blood cells into the now primed fluid circuit 20. Red blood cells are introduced into separator 30 through inlet 32 where they are separated into red blood cells and supernatant which may include plasma and a red blood cell additive/storage solution. The pores in membrane are sized such that separated red blood cells are not allowed to pass through the membrane. Instead, the red blood cells accumulate in the gap between the outer surface of the membrane and the inner surface of the separator housing, eventually exiting the separator through outlet 36 and flowing into "final" container 48. Supernatant passes through the membrane and is pumped by pump 16 through outlet 34 and into waste container 46. During processing, clamp 25 is open and the volume-reduced red blood cells collected in container 48 begin to drain from container 48, passing through filter 26 and are delivered to the patient 11.

Figure 9:
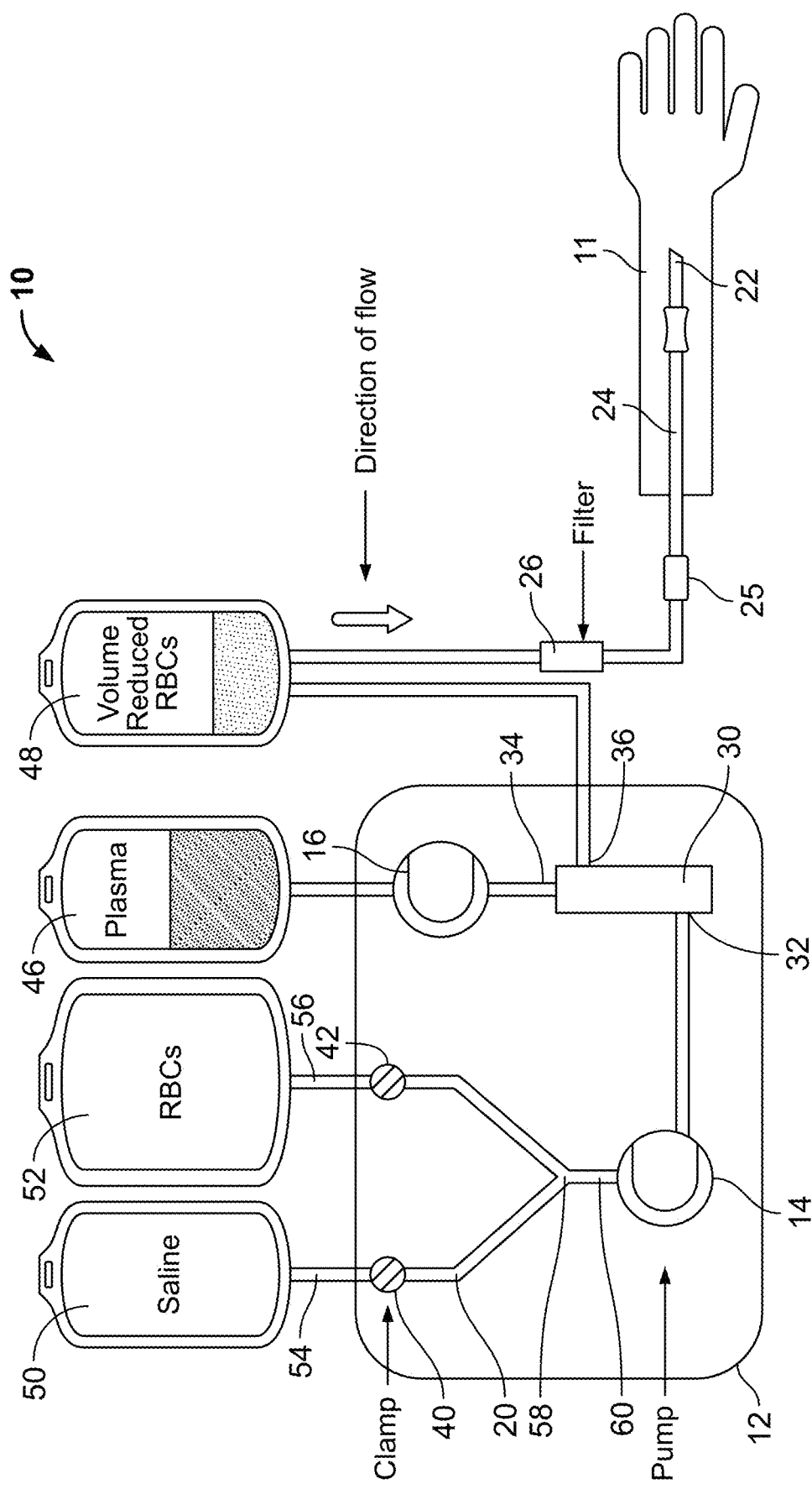
FIG. 9 is a schematic view of the system of FIG. 6 during the infusion of the volume-reduced red blood cells to the patient.
Figure 10:
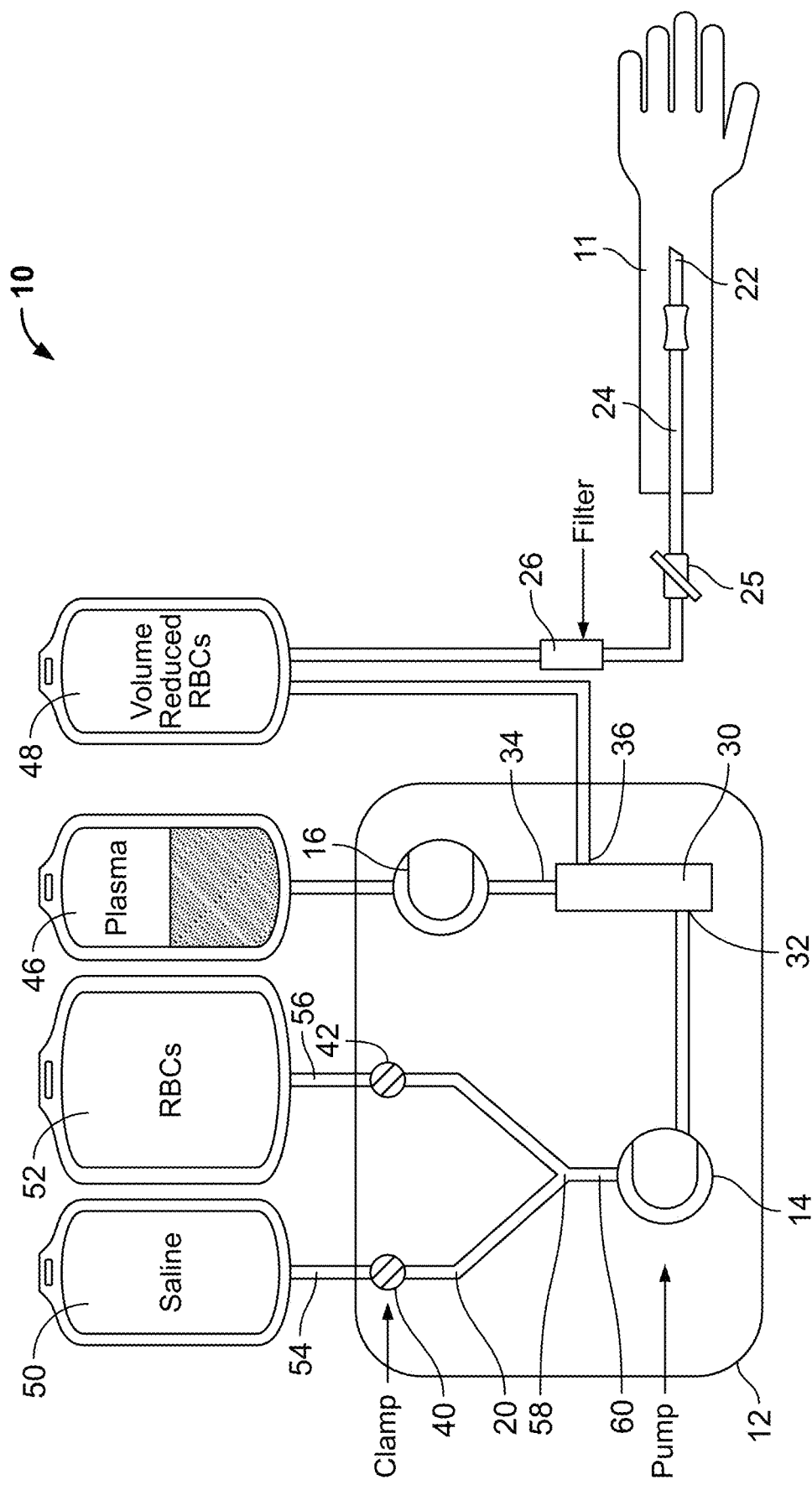
FIG. 10 is a schematic view of the system after infusion of the volume-reduced red blood cells to the patient.

Once the entire volume of previously collected red blood cells has been processed and container 52 is empty (which can be visually ascertained or determined by the change in weight of the container 52 which may be suspended from a weigh scale on apparatus 12), processing of the red blood cells from an original volume in container 52 to a reduced volume in container 48 is complete. As shown in FIG. 9, in this finishing phase, pumps 14 and 16 are turned off. With clamp 25 in an open position, a slow, gravity-fed infusion/transfusion of the reduced-volume red blood cells to the patient 11 which commenced during the previous processing phase continues. Once container 48 is empty as shown in FIG. 10, infusion/transfusion of the red blood cells is complete. In one embodiment, the volume of red blood cells can be reduced from, for example, a starting volume of 250 ml to a transfusible, reduced volume of 200 ml. Reducing the volume of supernatant remaining with the red blood cells "washes" the red blood cells and removes undesirable elements present in the original supernatant such as free hemoglobin.

Thus, an improved method and system have been disclosed for the processing of previously collected blood components such that the incidence of TACO can be reduced or avoided. The description provided above is intended for illustrative purposes only and is not intended to limit the scope of the invention to any specific method, system, or apparatus, or device described herein except as may be explicitly delineated above.

Aspects

Aspect 1. A method for transfusing a blood component to patient including accessing the vascular system of a patient with a needle in flow communication with a disposable fluid circuit mounted on an apparatus including a first pump, a second pump and a separation drive. The fluid circuit includes a container of priming solution, a waste container and a final reduced volume blood component container and a separation chamber. The method includes attaching a container of a collected blood component to the disposable fluid circuit; introducing a priming solution from the container of priming solution into at least a portion of the fluid circuit including the separation chamber; pumping the collected blood component from the container of the collected blood component into at least a portion of the fluid circuit including the separation chamber; separating the collected blood component into a reduced-volume blood component and a supernatant component in the separation chamber; collecting the supernatant in the waste container and collecting a volume reduced collected blood component in the final reduced volume blood component container; opening a flow path between the final reduced volume blood component container and the vascular system of the patient; and delivering a volume of the reduced collected blood component to the patient.

Aspect 2. The method of Aspect 1 including introducing the priming solution by activating said first pump.

Aspect 3. The method of Aspect 2 including collecting the supernatant in the waste container by activating the second pump to remove the supernatant through an outlet port of the separator.

Aspect 4. The method of any one of Aspects 1 through 3 wherein the separation chamber comprises a spinning membrane.

Aspect 5. The method of any one of Aspects 1 through 4 wherein the collected blood component comprises red blood cells.

Aspect 6. The method of any one of Aspects 1 through 4 wherein the collected blood component comprises platelets.

Aspect 7. The method of any one of Aspects 1 through 6 including pumping the collected blood component by activating said first pump.

Aspect 8. The method of any one of Aspects 1 through 7 including attaching a container of the collected blood component to the fluid circuit.

Aspect 9. The method of any one of Aspects 1 through 8 including selectively controlling flow of the priming solution and the collected blood component.

Aspect 10. The method of any one of Aspect 1 through further including filtering said volume reduced blood component between the steps of opening a flow path between the final reduced volume blood component container and the vascular system of the patient and delivering a volume of the reduced collected blood component to the patient.

Aspect 11. A system for transfusing a reduced-volume blood component to a patient comprising: a reusable separation and transfusion apparatus including a first pump, a second pump and a separator drive unit; a disposable fluid circuit associated with the reusable separation and transfusion apparatus, the fluid circuit including a vascular access device, a separation chamber, a final product container, a waste container and tubing defining flow paths between said containers and containers of a priming solution and collected blood component.

Aspect 12. The system of Aspect 11 wherein the first pump is associated with tubing defining a flow path to a container of a priming solution and tubing defining a flow path to a container of a previously collected blood component.

Aspect 13. The system of any one of Aspects 11 and 12 wherein said first pump is associated with tubing defining a flow path in communication with a separation chamber.

Aspect 14. The system of any one of Aspects 12 through 13 wherein the tubing defining a flow path to a container of a priming solution and the tubing defining a flow path to the container of the previously collected blood component are joined at a branching member.

Aspect 15. The system of Aspect 14 further including a first flow controller associated with the tubing defining a flow path to a container of a priming solution and a second flow controller associated with the tubing defining a flow path to the container of said previously collected blood component, the first and second flow controllers being located upstream of the branch member.

Aspect 16. The system of any one of Aspects 11 through 15 wherein the disposable fluid circuit further comprises a filter located between the final product container and the vascular access device.

Aspect 17. The system of Aspect 16 wherein the disposable fluid circuit further comprises a flow controller located between the filter and the vascular access device.

Aspect 18. The system of Aspect 17 wherein the flow controller is a manually operated clamp.

The invention claimed is:

1. A method for transfusing a blood component to a patient comprising:
   a) accessing a vascular system of a patient with a needle in flow communication with a disposable fluid circuit mounted on an apparatus including a first pump, a second pump and a separation drive, said fluid circuit comprising a container of priming solution, a waste container and a final reduced volume blood component container and a separation chamber;
   b) attaching a container of a previously collected blood component from a donor to said disposable fluid circuit;
   c) introducing a priming solution from said container of priming solution into at least a portion of said fluid circuit including said separation chamber;
   d) pumping said previously collected blood component from said container of said previously collected blood component into at least a portion of said fluid circuit including said separation chamber;
   e) separating said previously collected blood component into a reduced-volume blood component and a supernatant component in said separation chamber;
   f) collecting said supernatant in said waste container and collecting a volume reduced collected blood component in said final reduced volume blood component container;
   g) opening a flow path between said final reduced volume blood component container and said vascular system of said patient; and
   h) delivering said volume reduced collected blood component to said patient.

2. The method of claim 1 wherein comprising introducing said priming solution by activating said first pump.

3. The method of claim 2 comprising collecting said supernatant in said waste container by activating said second pump to remove said supernatant through an outlet port of said separator.

4. The method of claim 1 wherein said separation chamber comprises a spinning membrane.

5. The method of claim 1 wherein said previously collected blood component comprises red blood cells.

6. The method of claim 1 wherein said previously collected blood component comprises platelets.

7. The method of claim 1 comprising pumping said previously collected blood component by activating said first pump.

8. The method of claim 1 comprising selectively controlling flow of said priming solution and said previously collected blood component.

9. The method of claim 1 further comprising filtering said volume reduced blood component between steps (g) and (h).

\* \* \* \* \*